United States Patent
Zhang

(10) Patent No.: US 12,031,942 B2
(45) Date of Patent: Jul. 9, 2024

(54) METHOD AND DEVICE FOR DETERMINING THE AMMONIA CONCENTRATION AND THE NITROGEN MONOXIDE CONCENTRATION IN THE EXHAUST GAS FLOW OF A MOTOR VEHICLE

(71) Applicant: Vitesco Technologies GmbH, Hannover (DE)

(72) Inventor: Hong Zhang, Munich (DE)

(73) Assignee: VITESCO TECHNOLOGIES GMBH, Hannover (DE)

( * ) Notice: Subject to any disclaimer, the term of this patent is extended or adjusted under 35 U.S.C. 154(b) by 756 days.

(21) Appl. No.: 17/259,412

(22) PCT Filed: May 16, 2019

(86) PCT No.: PCT/EP2019/062738
§ 371 (c)(1),
(2) Date: Jan. 11, 2021

(87) PCT Pub. No.: WO2020/011427
PCT Pub. Date: Jan. 16, 2020

(65) Prior Publication Data
US 2021/0255138 A1    Aug. 19, 2021

(30) Foreign Application Priority Data
Jul. 12, 2018   (DE) ..................... 10 2018 211 572.9

(51) Int. Cl.
*G01N 27/419*    (2006.01)
*G01N 33/00*    (2006.01)

(52) U.S. Cl.
CPC ....... *G01N 27/419* (2013.01); *G01N 33/0037* (2013.01); *G01N 33/0054* (2013.01)

(58) Field of Classification Search
None
See application file for complete search history.

(56) References Cited

U.S. PATENT DOCUMENTS

| 4,770,760 A | 9/1988 | Noda et al. .................... 204/425 |
| 10,488,380 B2 | 11/2019 | Okamoto et al. |

(Continued)

FOREIGN PATENT DOCUMENTS

| DE | 3782584 T2 | 5/1993 | |
| DE | 10 2008 006 633 | 7/2009 | ........... G01N 27/409 |

(Continued)

OTHER PUBLICATIONS

Chinese Office Action, Application No. 201980046771.5, 14 pages, Sep. 2, 2022.

(Continued)

*Primary Examiner* — J. Christopher Ball
(74) *Attorney, Agent, or Firm* — Slayden Grubert Beard PLLC

(57) ABSTRACT

Various embodiments include a method of ascertaining the ammonia concentration and the nitrogen monoxide concentration in the exhaust gas stream from a motor vehicle comprising: measuring a pumping current at least three times; and determining an ammonia concentration and a nitrogen monoxide concentration based on three successive pumping current measurements.

9 Claims, 2 Drawing Sheets

(56) References Cited

U.S. PATENT DOCUMENTS

2009/0242426 A1* 10/2009 Kilinc .................. G01N 27/419
                                                        205/785.5
2019/0128833 A1*  5/2019 Nakagaki ............. G01N 27/419
2019/0137441 A1   5/2019 Nakagaki ............. G01N 27/407

FOREIGN PATENT DOCUMENTS

| DE | 102017122934 A1    | 12/2017 | ............. F01N 11/00   |
|----|---------------------|---------|----------------------------|
| DE | 102017007601 A1    |  4/2018 | ........... G01N 23/227    |
| EP | 3 477 291          |  5/2019 | ........... G01N 27/416    |
| JP | 09297119 A         | 11/1997 | ............. G01N 27/27   |
| WO | 2017 222001        | 12/2017 | ........... G01N 24/416    |
| WO | 2017 222002        | 12/2017 | ........... G01N 27/416    |
| WO | WO-2017222002 A1 * | 12/2017 | ............. F01N 11/007  |

OTHER PUBLICATIONS

Search Report for International Application No. PCT/EP2019/062738, 14 pages, Sep. 26, 2019.
Office Action for DE Application No. 10 2018 211 572.9, 6 pages, May 22, 2019.
Schönauer et al., "Selective Mixed Potential Ammonia Exhaust Gas Sensor," *Sensors and Actuators*, B 140, pp. 585-590, 2009.
DIN 1319-3:May 1996—Grundlagen der Messtechnik Volltext, 24 pages.
German Office Action, Application No. 102018211572.9, 4 pages.

* cited by examiner

METHOD AND DEVICE FOR DETERMINING THE AMMONIA CONCENTRATION AND THE NITROGEN MONOXIDE CONCENTRATION IN THE EXHAUST GAS FLOW OF A MOTOR VEHICLE

CROSS-REFERENCE TO RELATED APPLICATIONS

This application is a U.S. National Stage Application of International Application No. PCT/EP2019/062738 filed May 16, 2019, which designates the United States of America, and claims priority to DE Application No. 10 2018 211 572.9 filed Jul. 12, 2018, the contents of which are hereby incorporated by reference in their entirety.

TECHNICAL FIELD

The present disclosure relates to motor vehicles. Various embodiments of the teachings herein may include methods and/or devices for ascertaining the ammonia concentration and the nitrogen monoxide concentration in the exhaust gas stream from a motor vehicle.

BACKGROUND

WO 2017/222002 A1 describes a gas sensor and a method of measuring the concentrations of multiple components of a gas supplied. This gas sensor has three chambers arranged in succession, each connected to one another by a diffusion pathway. The first chamber is connected via a first diffusion pathway to a gas inlet, via which the gas sensor is supplied with the exhaust gas stream from a motor vehicle that includes nitrogen monoxide and ammonia. In a first mode of operation of the gas sensor, in which the first chamber is deactivated, the exhaust gas stream passes through the first chamber unchanged and is guided via a second diffusion pathway into the second chamber. The ammonia present in the exhaust gas stream is converted to nitrogen monoxide therein. This nitrogen monoxide is supplied to the third chamber together with further nitrogen monoxide present in the exhaust gas stream. Nitrogen monoxide is converted therein to nitrogen and oxygen, and a pumping current is measured. In a second mode of operation of the gas sensor in which the first chamber is activated, the ammonia present in the exhaust gas stream is converted to nitrogen monoxide actually within this first chamber. This nitrogen monoxide is in turn supplied to the third chamber together with further nitrogen monoxide present in the exhaust gas stream. Nitrogen monoxide is again converted therein to nitrogen and oxygen, and a pumping current is measured. Since the nitrogen monoxide transferred via the diffusion pathway envisaged between the first chamber and the second chamber and the ammonia have different coefficients of diffusion in the two aforementioned modes of operation, a corresponding pumping current value measured in the third chamber will likewise be different. The differential between the pumping current values measured, with use of empirically ascertained data recorded in a memory and recorded operating software, can be used individually to ascertain a corresponding nitrogen oxide concentration and a corresponding ammonia concentration.

SUMMARY

The teachings of the present disclosure include methods and apparatuses for ascertaining the ammonia concentration and the nitrogen monoxide concentration in the exhaust gas stream from a motor vehicle, which afford exact results even in dynamic operation of the motor vehicle. For example, some embodiments of the teachings herein may include a method of ascertaining the ammonia concentration and the nitrogen monoxide concentration in the exhaust gas stream from a motor vehicle, in which the ammonia concentration and nitrogen monoxide concentration are ascertained from at least three successive pumping current measurements.

In some embodiments, every two successive pumping current measurements are measured in different modes of operation of a nitrogen oxide sensor (1).

In some embodiments, the successive pumping current measurements are measured by means of a nitrogen oxide sensor (1) having an inlet for an exhaust gas stream, and having three chambers (5, 9, 13) arranged in series, with every two successive chambers connected to one another via a diffusion pathway (8, 12).

In some embodiments, in a first mode of operation, ammonia present in the exhaust gas stream and nitrogen monoxide present in the exhaust gas stream pass through the first chamber (5) unchanged and are supplied to the second chamber (9) via a diffusion pathway (8), the ammonia present in the exhaust gas stream is converted to nitrogen monoxide in the second chamber (9), and the nitrogen monoxide is supplied together with the nitrogen monoxide present in the exhaust gas stream to the third chamber (13) via a further diffusion pathway (12), and a corresponding pumping current value is measured in the third chamber (13).

In some embodiments, in a second mode of operation, ammonia present in the exhaust gas stream is converted to nitrogen monoxide in the first chamber (5), the nitrogen monoxide is supplied together with the nitrogen monoxide present in the exhaust gas stream to the second chamber (9) via a diffusion pathway (8), the nitrogen monoxide supplied to the second chamber (9) passes through the second chamber (9) and is supplied to the third chamber (13) via a further diffusion pathway (12), and a corresponding pumping current value is measured in the third chamber (13).

In some embodiments, the ammonia concentration and the nitrogen monoxide concentration are ascertained by means of a control unit (16) which is supplied with the three successive pumping current measurements.

In some embodiments, the control unit (16) ascertains the ammonia concentration and nitrogen monoxide concentration from four successive pumping current measurements, the first and third of which are measured in the first mode of operation and the second and fourth of which in the second mode of operation.

In some embodiments, the control unit (16) ascertains the ammonia concentration and nitrogen monoxide concentration on the basis of the following relationships:

$$NOx\_1 + s1 \cdot NH3\_1 = y1,$$

$$NOx\_2 + NH3\_2 = y2,$$

$$NOx\_3 + s1 \cdot NH3\_3 = y3 \text{ and}$$

$$NOx\_4 + NH3\_4 = y4,$$

where y1, y2, y3 and y4 are the successive pumping current measurements ascertained, each multiplied by a constant.

In some embodiments, the control unit (16) ascertains the ammonia concentration and the nitrogen monoxide concentration under the assumption that either the ammonia concentration or the nitrogen monoxide concentration will vary, and the variation will take place within a period of time required for a change of mode, by the following relationships:

$$NH3\_2=(y1+y3-2y2)/2\cdot(s1-1),$$

$$NOx\_2=y2-NH3\_2,$$

$$NH3\_3=(2y3-y2-y4)/(2\cdot(s1-1)) \text{ and}$$

$$NOx\_4=y3-s1\cdot NH3\_3.$$

As another example, some embodiments include a device for ascertaining the ammonia concentration and the nitrogen monoxide concentration in the exhaust gas stream from a motor vehicle, having a control unit (16) that ascertains the ammonia concentration and nitrogen monoxide concentration from at least three successive pumping current measurements.

In some embodiments, the control unit (16) ascertains the ammonia concentration and nitrogen monoxide concentration from four successive pumping current measurements.

BRIEF DESCRIPTION OF THE DRAWINGS

Further details of the teachings herein are apparent from the illustrative description thereof with reference to the drawings.

DETAILED DESCRIPTION

In various methods incorporating teachings of the present disclosure for ascertaining the ammonia concentration and nitrogen monoxide concentration in the exhaust gas stream from a motor vehicle, the concentrations mentioned are ascertained using at least three pumping current measurements that are ascertained successively in time in two different modes of operation of the nitrogen oxide sensor.

Ascertaining the concentrations mentioned in such a way allows these concentrations to be ascertained individually and accurately in dynamic operation of the motor vehicle, with the possibility that variations occur in the nitrogen monoxide concentration and/or the ammonia concentration in this dynamic operation.

Figure 1:
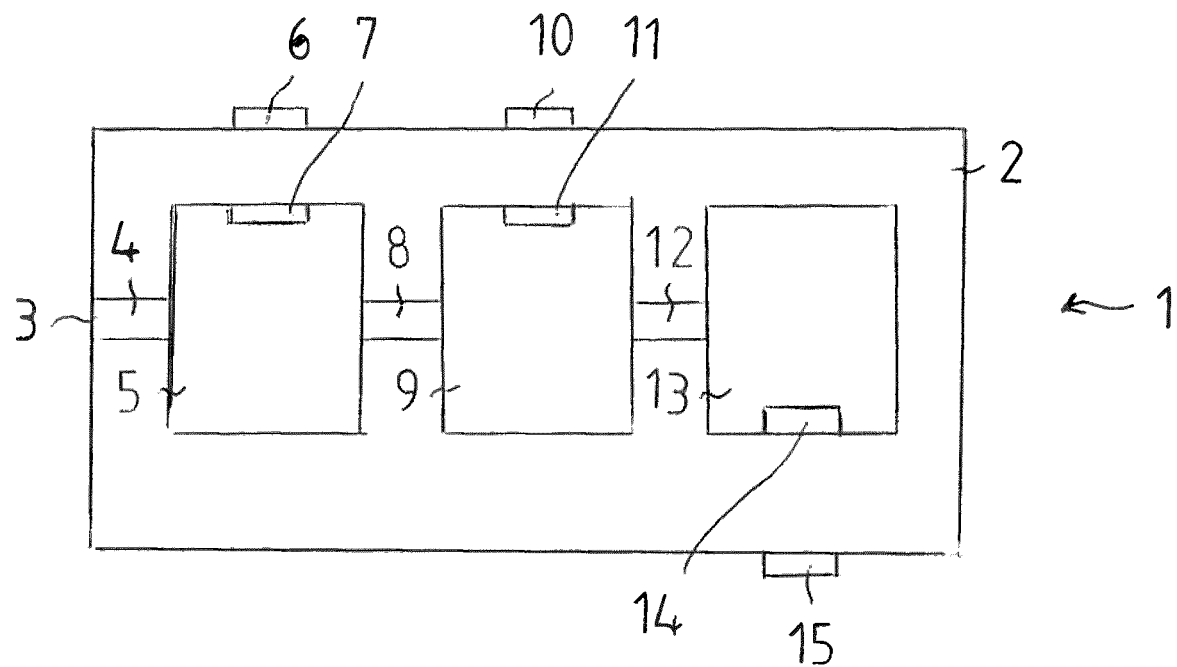
FIG. 1 is a block diagram of a nitrogen oxide sensor that can be used to implement a method incorporating teachings of the present disclosure.
Figure 1:
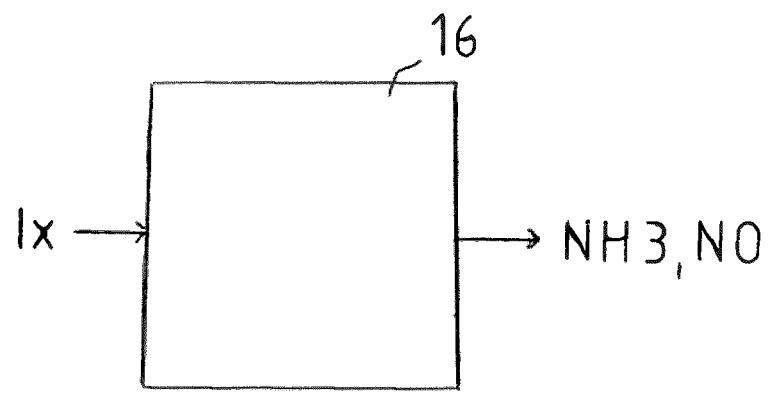

FIG. 1 is a block diagram showing a nitrogen oxide sensor that can be used to implement the methods taught herein. This nitrogen oxide sensor 1 contains a sensor body 2 having an inlet 3 for the exhaust gas stream from a motor vehicle. This inlet 3 is connected via a first diffusion pathway 4 to a first chamber 5. Assigned to the first chamber 5 are electrodes 6 and 7, to which a voltage can be applied by means of a control unit 16 in order to activate this chamber.

The outlet from the first chamber 5 is connected via a second diffusion pathway 8 to a second chamber 9 to which electrodes 10 and 11 are assigned.

The outlet from the second chamber 9 is connected via a third diffusion pathway 12 to a third chamber 13. This third chamber has assigned electrodes 14 and 15. This third chamber 13 is a measurement chamber in which a pumping current measurement can be conducted using the electrodes 14 and 15. The pumping current values Ix measured are sent to a control unit 16 that uses these pumping current measurements, in accordance with a recorded working program using further recorded data, to ascertain the ammonia concentration and nitrogen monoxide concentration of the exhaust gas supplied to the inlet 3 of the nitrogen oxide sensor 1.

The nitrogen oxide sensor 1 shown in FIG. 1 has at least two modes of operation. In the first mode of operation, the first chamber 5 is deactivated. In this first mode of operation, the ammonia present in the exhaust gas stream and the nitrogen monoxide present in the exhaust gas stream pass through the first chamber 5 unchanged and are supplied to the second chamber 9 via the second diffusion pathway 8. In this second chamber 9, the ammonia present in the exhaust gas stream is converted to form nitrogen monoxide according to the following relationship:

$$4NH_3+5O_2 \rightarrow 4NO+6H_2O.$$

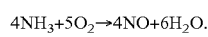

The nitrogen monoxide formed, together with the further nitrogen monoxide present in the exhaust gas stream, is passed on via the third diffusion pathway 12 into the third chamber 13. The pumping current is measured therein. The pumping current measurement is sent to the control unit 16. In addition, in the third chamber 13, the nitrogen monoxide is converted to nitrogen and oxygen, which are released to the environment via the tailpipe of the exhaust gas conduit of the motor vehicle.

In the second mode of operation, the first chamber 5 is activated. In this second mode of operation, the ammonia present in the exhaust gas stream is already converted in the first chamber 5 to form nitrogen monoxide according to the following relationship:

$$4NH_3+5O_2 \rightarrow 4NO+6H_2O.$$

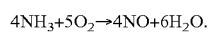

The nitrogen monoxide formed, together with the further nitrogen monoxide present in the exhaust gas stream, is passed on via the second diffusion pathway 8 into the second chamber 9. The nitrogen monoxide supplied to the second chamber 9 passes through the second chamber 9 unchanged and is supplied via the third diffusion pathway 12 to the third chamber 13. The pumping current is measured therein. The pumping current measurement is sent to the control unit 16. In addition, in the third chamber 13, the nitrogen monoxide is converted to nitrogen and oxygen, which are released to the environment via the tailpipe of the exhaust gas conduit of the motor vehicle.

The pumping current values measured in the two modes of operation described will be different on account of the different coefficients of diffusion of ammonia and nitrogen monoxide. This pumping current differential is ascertained in the control unit 16 and, taking additional account of operating software recorded and further data recorded, used to ascertain the ammonia concentration and nitrogen monoxide concentration in the exhaust gas stream.

For this ascertainment of the ammonia concentration and nitrogen monoxide concentration, at least 3 successive pumping current measurements are used, where every two successive pumping current measurements are measured in different modes of operation of the nitrogen oxide sensor.

In the case of use of 3 pumping current measurements, for example, the first pumping current measurement is measured in the first mode of operation, the second pumping current measurement in the second mode of operation, and the third pumping current measurement in the first mode of operation again.

In some embodiments, in the case of use of 3 pumping current measurements, the first pumping current measurement can be measured in the second mode of operation, the second pumping current measurement in the first mode of operation, and the third pumping current measurement in the second mode of operation again.

In the case of use of 4 pumping current measurements, for example, the first pumping current measurement is measured in the first mode of operation, the second pumping current measurement in the second mode of operation, the third pumping current measurement in the first mode of operation again, and the fourth pumping current measurement in the second mode of operation again.

In some embodiments, in the case of use of 4 pumping current measurements, the first pumping current measurement can be measured in the second mode of operation, the second pumping current measurement in the first mode of operation, the third pumping current measurement in the second mode of operation again, and the fourth pumping current measurement in the first mode of operation again.

The use of at least three successive pumping current measurements achieves the effect that, even in the case of dynamic operation in which the ammonia concentration and/or the nitrogen monoxide concentration vary within a short time, the ammonia concentration and nitrogen monoxide concentration can be ascertained with high accuracy.

In the case of ascertainment of the ammonia concentration and nitrogen monoxide concentration from four successive pumping current measurements, the ascertaining of the concentrations mentioned is based on the following relationships:

$$NOx\_1 + s1 \cdot NH3\_1 = y1, \quad (1)$$

$$NOx\_2 + NH3\_2 = y2, \quad (2)$$

$$NOx\_3 + s1 \cdot NH3\_3 = y3 \quad (3) \text{ and}$$

$$NOx\_4 + NH3\_4 = y4, \quad (4)$$

where y1, y2, y3 and y4 are the successive pumping current measurements ascertained, each multiplied by a constant. y1 and y3 were determined here in the first mode of operation, and y2 and y4 in the second mode of operation.

Assuming that there is variation between the two modes of operation mainly either in the nitrogen monoxide concentration or in the ammonia concentration and that the variation is linear within the short period of time of the change of mode, the above-stated relationships can be resolved as follows:

$$NH3\_2 = (y1 + y3 - 2y2)/2 \cdot (s1 - 1) \quad (5),$$

$$NOx\_2 = y2 - NH3\_2 \quad (6),$$

$$NH3\_3 = (2y3 - y2 - y4)/(2 \cdot (s1 - 1)) \quad (7) \text{ and}$$

$$NOx\_4 = y3 - s1 \cdot NH3\_3 \quad (8).$$

Consequently, the relationships reproduced above can be used in the sequence specified alternately for the first mode of operation and the second mode of operation for exact ascertainment of the ammonia concentration and the nitrogen monoxide concentration in the exhaust gas from a motor vehicle. The accuracy of the ascertainment is based here more particularly on inclusion of at least one third pumping current measurement in the ascertaining of the concentrations mentioned.

Figure 2:
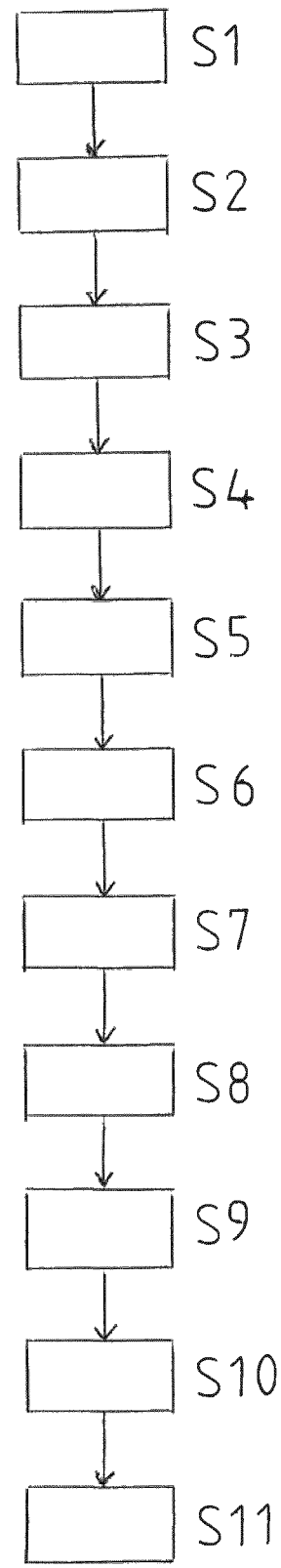
FIG. 2 is a flow diagram for elucidation of a working example of a method incorporating teachings of the present disclosure.

FIG. 2 shows a flow diagram outlining a method of ascertaining the ammonia concentration and the nitrogen monoxide concentration in the exhaust gas stream from a motor vehicle incorporating teachings of the present disclosure.

The method begins with a step S1.

Thereafter, in a step S2, the nitrogen oxide sensor is switched into the first mode of operation in which the first chamber 5 is deactivated. This is followed, in a step S3, by a measurement of the pumping current in the third chamber 13, and the pumping current value measured is passed onward to the control unit 16.

The method then moves to step S4 in which the nitrogen oxide sensor is switched over into the second mode of operation in which the first chamber 5 is activated. This is followed, in a step S5, by a measurement of the pumping current in the third chamber 13, and the pumping current value measured is passed onward to the control unit 16.

Thereafter, the method moves to step S6 in which the nitrogen oxide sensor is switched over into the first mode of operation in which the first chamber 5 is deactivated. After this switchover, in a step S7, the pumping current is measured in the third chamber 13, and the pumping current value measured is passed onward to the control unit 16.

The method then moves to step S8 in which the nitrogen oxide sensor is switched over into the second mode of operation in which the first chamber 5 is activated. This is followed, in a step S9, by a measurement of the pumping current in the third chamber 13, and the pumping current value measured is passed onward to the control unit 16.

After step S9, the method moves to a step S10 in which the control unit 16 ascertains exact values for the ammonia content and nitrogen oxide content of the exhaust gas stream according to the above-stated relationships 5, 6, 7 and 8 using the pumping current values measured, a recorded working program and further data recorded.

The method ends with a subsequent step S11.

The invention claimed is:

1. A method of ascertaining the ammonia concentration and the nitrogen monoxide concentration in an exhaust gas stream from a motor vehicle, the method comprising:
   delivering the exhaust gas stream to a gas sensor with three chambers in series;
   measuring a pumping current in a third chamber of the three chambers at least three times; and
   determining an ammonia concentration and a nitrogen monoxide concentration based on three successive pumping current measurements.

2. The method as claimed in claim 1, wherein every two successive pumping current measurements are measured in different modes of operation of a nitrogen oxide sensor.

3. The method as claimed in claim 1, wherein:
   the pumping current measurements are measured using a nitrogen oxide sensor having an inlet for an exhaust gas stream and three chambers arranged in series; and
   every two successive chambers connected to one another via a diffusion pathway.

4. The method as claimed in claim 3, wherein:
   in a first mode of operation, ammonia present in the exhaust gas stream and nitrogen monoxide present in the exhaust gas stream pass through the first chamber unchanged and are supplied to the second chamber via a diffusion pathway;
   the ammonia present in the exhaust gas stream is converted to nitrogen monoxide in the second chamber;
   the nitrogen monoxide is supplied together with the nitrogen monoxide present in the exhaust gas stream to the third chamber via a further diffusion pathway; and
   a corresponding pumping current value is measured in the third chamber.

5. The method as claimed in claim 3, wherein, in a second mode of operation:
- ammonia present in the exhaust gas stream is converted to nitrogen monoxide in the first chamber;
- the nitrogen monoxide is supplied together with the nitrogen monoxide present in the exhaust gas stream to the second chamber via a diffusion pathway;
- the nitrogen monoxide supplied to the second chamber passes through the second chamber and is supplied to the third chamber via a further diffusion pathway; and
- a corresponding pumping current value is measured in the third chamber.

6. The method as claimed in claim 1, wherein the ammonia concentration and the nitrogen monoxide concentration are ascertained by a control unit supplied with the three successive pumping current measurements.

7. The method as claimed in claim 6, wherein the control unit ascertains the ammonia concentration and nitrogen monoxide concentration from four successive pumping current measurements, the first and third of which are measured in the first mode of operation and the second and fourth of which in the second mode of operation.

8. The method as claimed in claim 7, wherein the control unit ascertains the ammonia concentration and nitrogen monoxide concentration on the basis of the following relationships:

$$NOx\_1 + s1 \cdot NH3\_1 = y1,$$

$$NOx\_2 + NH3\_2 = y2,$$

$$NOx\_3 + s1 \cdot NH3\_3 = y3 \text{ and}$$

$$NOx\_4 + NH3\_4 = y4,$$

wherein y1, y2, y3, and y4 are the successive pumping current measurements ascertained, each multiplied by a constant;

wherein $NOx\_1$, $NOx\_2$, $NOx\_3$, and $NOx\_4$ are successive nitrogen monoxide concentrations and $NH3\_1$, $NH3\_2$, $NH3\_3$, and $NH3\_4$ are successive ammonia concentrations.

9. The method as claimed in claim 7, wherein the control unit ascertains the ammonia concentration and the nitrogen monoxide concentration based on an assumption that either the ammonia concentration or the nitrogen monoxide concentration will vary, and the variation will take place within a period of time required for a change of mode, by the following relationships:

$$NH3\_2 = (y1 + y3 - 2y2)/2 \cdot (s1-1),$$

$$NOx\_2 = y2 - NH3\_2,$$

$$NH3\_3 = (2y3 - y2 - y4)/(2 \cdot (s1-1)) \text{ and}$$

$$NOx\_4 = y3 - s1 \cdot NH3\_3;$$

wherein $NOx\_1$, $NOx\_2$, $NOx\_3$, and $NOx\_4$ are successive nitrogen monoxide concentrations and $NH3\_1$, $NH3\_2$, $NH3\_3$, and $NH3\_4$ are successive ammonia concentrations.

* * * * *